United States Patent
Cinelli et al.

(10) Patent No.: US 6,544,642 B2
(45) Date of Patent: Apr. 8, 2003

(54) DISPOSABLE ABSORBENT ARTICLES WITH IMPROVED ADHESIVE FOR ATTACHMENT TO THE SKIN TO FACILITATE ADHESION IN OILY CONDITIONS

(75) Inventors: Fabio Cinelli, Bologna (IT); Antonello Colaianni, Pescara (IT); Adelia Alessandra Tordone, Pescara (IT); Hugh Semple Munro, Chipping Camden (GB); Brian John Tighe, Aston Triangle (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/917,577

(22) Filed: Jul. 27, 2001

(65) Prior Publication Data

US 2002/0012792 A1 Jan. 31, 2002

Related U.S. Application Data

(63) Continuation of application No. PCT/US00/02769, filed on Feb. 2, 2000.

(30) Foreign Application Priority Data

Feb. 2, 1999 (EP) ............................................. 99102051

(51) Int. Cl.⁷ ................................................ B32B 7/12
(52) U.S. Cl. ....................... 428/343; 525/56; 525/92 A; 525/185; 525/218; 525/222; 525/105; 524/366; 524/387
(58) Field of Search ................................. 524/387, 366; 525/56, 92 A, 185, 218, 222; 523/105

(56) References Cited

U.S. PATENT DOCUMENTS

| | | |
|---|---|---|
| 3,577,989 A | 5/1971 | Anderson |
| 3,929,135 A | 12/1975 | Thompson |
| 4,324,246 A | 4/1982 | Mullane et al. |
| 4,342,314 A | 8/1982 | Radel et al. |
| 4,463,045 A | 7/1984 | Ahr et al. |
| 4,593,053 A * | 6/1986 | Jevne et al. ................. 523/111 |
| 4,609,518 A | 9/1986 | Curro et al. |
| 4,629,643 A | 12/1986 | Curro et al. |
| 4,699,146 A * | 10/1987 | Sieverding ................... 128/640 |
| 4,784,656 A | 11/1988 | Christian |
| 5,006,394 A | 4/1991 | Baird |
| 5,015,244 A | 5/1991 | Cross |
| 5,147,338 A * | 9/1992 | Lang et al. ................... 604/304 |
| 5,173,302 A * | 12/1992 | Holmblad et al. ........... 424/448 |
| 5,338,490 A * | 8/1994 | Dietz et al. .................. 252/500 |
| H1602 H | 10/1996 | Brock |
| 5,670,557 A * | 9/1997 | Dietz et al. .................. 522/184 |
| 5,728,146 A | 3/1998 | Burkett et al. |
| 5,741,318 A | 4/1998 | Ouellette et al. |
| 6,177,482 B1 * | 1/2001 | Cinelli et al. ................ 523/111 |
| 6,191,189 B1 * | 2/2001 | Cinelli et al. ................ 523/111 |
| 6,198,017 B1 | 3/2001 | Basedow et al. |
| 6,211,263 B1 * | 3/2001 | Cinelli et al. ................ 523/111 |
| 6,365,645 B1 * | 4/2002 | Cinelli et al. ................ 523/105 |
| 6,369,126 B1 * | 4/2002 | Cinelli et al. ................ 523/105 |
| 2002/0015689 A1 * | 2/2002 | Munro et al. ............. 424/78.31 |

FOREIGN PATENT DOCUMENTS

| | | | |
|---|---|---|---|
| CH | 643730 A1 | 11/1980 | |
| EP | 245064 A2 | 11/1987 | |
| EP | 184470 B1 | 4/1991 | |
| EP | 554106 A1 | 8/1993 | |
| EP | 554 106 A1 * | 8/1993 | ............ C09J/15/10 |
| EP | 753290 A2 | 1/1997 | |
| EP | 638303 B1 | 11/1997 | |
| EP | 850625 A1 | 7/1998 | |
| EP | 850649 A1 | 7/1998 | |
| EP | 850 649 A1 * | 7/1998 | ............ A61L/15/58 |
| EP | 855190 A1 | 7/1998 | |
| EP | 676457 B1 | 10/1998 | |
| EP | 888786 A2 | 1/1999 | |
| EP | 1 026 219 A1 * | 8/2000 | ............ C09J/210/02 |
| GB | 1078588 | 5/1966 | |
| GB | 2115431 A1 | 9/1983 | |
| GB | 2152387 A1 | 8/1985 | |
| WO | WO 93/09744 A1 | 5/1993 | |
| WO | WO 93/10201 A1 | 5/1993 | |
| WO | WO 93/11725 A1 | 6/1993 | |
| WO | WO 93/11726 A1 | 6/1993 | |
| WO | WO 95/16424 A1 | 6/1995 | |
| WO | WO 95/20634 A1 | 8/1995 | |
| WO | WO 96/13238 A1 | 5/1996 | |
| WO | WO 96/33683 A1 | 10/1996 | |
| WO | WO 97/01311 A1 | 1/1997 | |
| WO | WO 97/05171 A1 | 2/1997 | |
| WO | WO 97/24149 A1 | 7/1997 | |
| WO | WO 97/36968 A1 | 10/1997 | |
| WO | WO 97/49361 A1 | 12/1997 | |
| WO | WO 98/03208 A1 | 1/1998 | |
| WO | WO 98/27914 A1 * | 7/1998 | ............ A61F/13/15 |
| WO | WO 98/28016 A1 * | 7/1998 | ............ A61L/15/58 |
| WO | WO 98/28017 A1 * | 7/1998 | ............ A61L/15/58 |
| WO | WO 98/28021 A1 * | 7/1998 | ............ A61L/15/58 |
| WO | WO 99/00092 A1 | 1/1999 | |
| WO | WO 00/45766 A1 | 8/2000 | |
| WO | WO 00/45863 A1 | 8/2000 | |
| WO | WO 00/45865 A1 | 8/2000 | |
| WO | WO 00/45866 A1 | 8/2000 | |

\* cited by examiner

Primary Examiner—David W. Wu
Assistant Examiner—Rip A Lee
(74) Attorney, Agent, or Firm—Peter D. Meyer

(57) ABSTRACT

The present invention relates to a disposable absorbent articles such as diapers and sanitary napkins which are provided with adhesives for attachment of the article to the skin. In particular the present invention relates to adhesives which provide secure attachment and are pleasing to the skin upon application, yet cause no discomfort upon removal. In particular the present invention relates to an adhesive which provide secure attachment to oily and greasy skin. Preferably the adhesive also provides secure attachment under moist and wet skin conditions and which maintains adhesive peel strength even under exposure to excess water.

16 Claims, No Drawings

DISPOSABLE ABSORBENT ARTICLES WITH IMPROVED ADHESIVE FOR ATTACHMENT TO THE SKIN TO FACILITATE ADHESION IN OILY CONDITIONS

PRIOR APPLICATION

This application is a continuation of PCT Application No. PCT/US00/02769 filed on Feb. 2, 2000 and published in English.

FIELD OF THE INVENTION

The present invention relates to a disposable absorbent articles such as diapers, sanitary napkins, pantiliners, tampons, perspiration pads, adult incontinence devices and the like to be attached directly to the skin of the wearer. The articles utilise an improved adhesive so as to facilitate easy application and removal of the article from the wearer, whilst ensuring maintenance of the article in the desired position. In particular the adhesives provide attachment on greasy and oily skin.

BACKGROUND OF THE INVENTION

The present invention relates to adhesives which are particularly useful to absorbent articles for absorption of body liquids which naturally emanate from a body without a wound. For example to attach diapers, sanitary napkins or pantiliners in the genital region. Also incontinence devices which are worn e.g. in the genital region or perspiration pads which are worn in the arm pit region of a person can suitably employ the adhesive of the present invention.

Such adhesives have been generally disclosed in for example US statutory invention registration H1602 or WO 96/33683 and WO 95/16424. The latter discloses sanitary articles having a topical adhesive which is applied on the wearer facing side of a sanitary napkin along the entire periphery. WO 96/13238 discloses a topical adhesive which is described in terms of frequency dependency. EP-638 303 discloses the use of a topical adhesive on side cuffs of sanitary napkins in order to keep the cuffs in an upright position. Swiss publication CH-643730 discloses the use of a very long sanitary napkin having chamfered outer edges with a topical adhesive at the four corners of the outer edges in order to provide a topical adhesive area well outside the region of pubic hair growth.

However all of these disclosures typically disclose a product which is designed to be utilised in combination with an undergarment and hence the degree of adhesion actually provided is very low and is not designed to withstand any excessive pressure. Moreover the adhesive is only discussed in general terms or concentrates on the area of application of the adhesive to the article. The nature of adhesive per se other than the basic physical requirements such as pressure sensitivity are not discussed in particular with reference to the chemical composition or the adhesive criteria.

The prior art in the general field of adhesives for attachment to the skin is particularly developed in the field of articles such as band-aids, plasters and bandages. These articles are however typically applied in an emergency situation, where for example, a cut into the skin of the wearer has occurred and absorption of the body liquids emanating from a wound is desired. In this context performance aspects of the article such as easy application and use of the product, comfortable wear as well as painless removal, and discreteness are again subordinate, to other criteria in this case such as sterility, healing support, and mechanical protection of the wound. Also such wound covering absorbent articles are mostly adhered to the skin where prior to application of the absorbent article bodily hair can be removed or where little hair grows.

In order to provide the desired level of adhesion of such bandages, the prior art typically discloses the utilisation of certain adhesives having very high cohesive strengths such as rubber based adhesives and acrylics. These adhesives are then applied as thick layers to maximise the adhesive force by which the bandage is secured to the skin of the wearer.

U.S. Pat. No. 4,699,146 discloses hydrophilic elastomeric pressure sensitive adhesives suitable for use with ostomy devices, bandages, ulcer pads, sanitary napkins, diapers, and althetic padding. The adhesive comprises at least 1 radiation cross linked organic polymer and an adhesive plasticizer.

GB 2 115 431 discloses adhesives for bandages, wounds or burn dressings, EKG adhesives, sanitary napkins, diapers and ulcer pads. The adhesive comprises an irradiation cross-linked organic polymer such as polyvinylpyrrolidone and an adhesive plasticizer.

However, for application such as absorbent articles it is important that the adhesive has a skin compatible composition and not be harsh or aggressive towards the skin or cause skin irritation or inflammation. Also it is preferred if the adhesive is compliant with the skin of the wearer such that maximum skin surface contact between the adhesive and the skin is achieved. Moreover, it is also desirable to provide an adhesive such that the absorbent article can be readily removed from the wearer, without the wearer experiencing any unacceptable pain level. This is particularly important under circumstances, where the article is removed and reapplication of the article once or even a number of times is required for example to allow for urination and or to ensure the application of such articles on sensitive skin and wearer groups such as infants. However, on the other hand the desired level of adhesion, albeit painless should of course also be maintained during such multiple applications of the article.

The problem of achieving the desired adhesion level is further exacerbated under wet skin conditions. Typically, prior to the placement of the article the skin is cleaned and is usually as a result moist. The currently available adhesives, such as those containing hydrocolloid particles, however often do not immediately strongly adhere to the skin and may need to be held in place until sufficient minimum adhesion occurs. Moreover, the overall adhesive ability of such adhesives tends to be significantly reduced on wet skin surfaces per se, so that the article will typically not remain attached to the skin during wearer if any pressure is exerted onto the article, for example by the movement of the wearer.

Moist and wet skin however is not just a problem which is prevalent at the article application stage as a significant amount of moisture is also generated during the use of the article from the wearer by perspiration and from bodily fluids. Under such circumstances currently available adhesives typically cannot absorb this moisture and again the adhesive strength is reduced to such an extent that the article will often become detached under exertion of pressure during wear. It is hence very important to provide an adhesive which provides both initial adhesion and maintenance of its adhesive strength on wet skin. Moreover, it is also another important factor for the product performance that the adhesive is also stable to exposure to excess quantities of liquid such as water, urine and menstrual fluids and will also not lose its adhesive strength under such circumstances.

Another problem which is particularly prevalent for absorbent article usage is the ability of the adhesive to adhere on greasy or oily skin surfaces. The levels and types of grease and sebum naturally present on the skin vary from person to person. In addition, the wearers of such articles typically utilise creams such as moisturising creams, rash creams or other pharmaceutical creams on the area of skin typically in contact with the adhesive of the article. Thus it is also highly desirable that the adhesive exhibits an ability to adhere to greasy skin.

None of the prior art in the field of absorbent articles however even recognises or addresses the problem of providing these devices with an adhesive which meets these criteria, in particular adhesives which adhere to wet skin and are stable and maintain their adhesiveness even when exposed to excessive amounts of liquid, or adhesives which adhere to oily and greasy skin.

Adhesion to wet skin is addressed for example in WO 98/03208 which discloses medical pressure sensitive adhesives which can adhere to dry or wet skin and which comprise a mixture of hydrophilic (meth)acrylate copolymer containing tertiaryamino groups, a hydrophilic (meth)acrylate copolymer containing carboxyl groups, carboxylic acids and a crosslinking system. However this document does not discuss adhesion after exposure to excess liquid.

However, there still exists a need to disposable absorbent articles having an adhesive for the secure attachment and painless removal of the article from the skin suitable for use of sensitive skin of an infant and or of the genitalia and it is thus an object of the present invention to provide such an article.

It is another objective of the present invention to provide an adhesive that exhibits an ability to adhere to skin upon reapplication, particularly multiple reapplication for example when the article is removed for urination purposes or is misplaced, whilst still allowing painless removal.

It is another object of the present invention to provide an adhesive that will adhere to oily and greasy skin, preferably over the entire period of wear.

It is yet a further objective of the present invention that the adhesive will adhere to moist or wet skin, independent of whether this is direct application of the article onto wet skin, or moisture which is generated on the skin surface during the wearing period of the article. In particular it is an objective of the present invention to provide an adhesive which is liquid stable particularly to water and urine, such that the adhesion properties will not be significantly effected in the presence thereof over the period of wear of the article.

It is another object of the present invention to provide an adhesive which upon removal from the skin of the wearer leaves no residues. It is yet another object of the present invention to provide an adhesive which does not cause a cold or otherwise unacceptable temperature sensation upon application to the wearer.

An additional object of the present invention to provide an adhesive which provides flexibility, stretchability and contractability so that it is able to adapt to the contours of the body during all bodily movements and hence be comfortable for the wearer of the article, whilst still having sufficient adhesive capacity to ensure secure attachment during use.

It has now been surprisingly found that the above drawbacks will be substantially alleviated by providing the absorbent article with an adhesive as defined hereinafter. The adhesive provides secure attachment, is pleasing to the skin upon application including to moist and oily surfaces, and yet causes no discomfort upon removal and maintains its adhesive strength over the period of wear, under varying conditions.

SUMMARY OF THE INVENTION

Any disposable absorbent article known in the art can be provided with the adhesive according to the present invention. According to the present invention the adhesive is provided so as to have an initial dry skin peel strength ($P_{DI}$) and an initial greasy skin peel strength ($P_{GI}$) measured according to the test method herein, which has a ratio of $P_{DI}$ to $P_{GI}$ of from 1:1 to 1:0.2, preferably from 1:1 to 1:0.3.

According to the present invention the adhesive is also preferably provided so as to have an initial peel strength ($P_{DI}$) under normal ambient conditions and a final peel strength ($P_{WF}$) after exposure to water according to the test method described herein, whereby the ratio of $P_{DI}$ to $P_{WF}$ is from 2:1 to 1:4 preferably from 2:1.25 to 2:4 and has a water absorption capacity as defined in the test herein of at least 3% by weight of said adhesive.

The adhesive allows attachment of disposal absorbent articles to the skin of the wearer, the adhesive being provided as a layer having a certain thickness or caliper C measured in millimetres (mm), typically on at least part of the wearer facing surface of the article.

Detailed analysis of the sequence of common situations occurring from the application of absorbent articles to the time of removal of such articles has shown that specific adhesive characteristics need to be preferably satisfied in order to achieve the desired performance objectives, in particular to secure initial attachment, secure attachment during use and painless removal after wear. The characteristics which have been considered in this context are the elastic modulus describing the elastic behaviour of the material and the viscous modulus which describes the viscous behaviour of the adhesive material.

The viscous behaviour of the adhesive can be interpreted to represent an indication of the ability of the adhesive to quickly attach and securely adhere to a particular surface. The elastic behaviour can be interpreted as an indication of the "hardness" behaviour of the adhesive. Its value is also important for good initial attachment. Their combination is believed to be an indicator of the required force upon removal. The relation between elastic and viscous modulus is considered to be an indication on which fraction of the removal energy will be dissipated within the adhesive and which fraction is available to trigger the actual removal.

In order to provide adhesives for secure initial and prolonged attachment and easy/painless removal the relation between the elastic modulus and the viscous modulus as well as their dynamic behaviour is also of importance.

The adhesive has an elastic modulus at a temperature of 37° C. (100° Fahrenheit) abbreviated $G'_{37}$, a viscous modulus at a temperature of 37° C. (100° Fahrenheit) of $G''_{37}$, and a viscous modulus at a temperature of 25° C. (77° Fahrenheit) of $G''_{25}$.

The adhesive according to the present invention preferably satisfies the following conditions;

| | |
|---|---|
| $G'_{37}$(1 rad/sec) | is in the range 500 Pa to 20000 Pa, preferably 700 Pa to 15000 Pa, most preferably 1000 Pa to 10000 Pa. |
| $G''_{37}$(1 rad/sec) | is in the range 100 Pa to 15000 Pa, preferably 100 Pa to 10000 Pa, most preferably 300 Pa to 5000 Pa. | and the ratio of $G'_{37}$ (1 rad/sec)/$G''_{37}$ (1 rad/sec) is in the range of 1 to 30.

Provided the above rheological conditions are satisfied the adhesives will also satisfy conditions such as sufficient cohesiveness (to prevent residue of adhesive on the skin) which are important for commercial use of such adhesives and apparent to those skilled in the art. Adhesive compositions which satisfy the above criteria can be used as adhesives for the article provided they also satisfy the common requirements of being safe for use on human or animal skin during use and generally after disposal of the device.

Often the criteria of hygienic appearance such that adhesive compositions which are transparent or white upon application are preferred.

It has been determined that the relation between the thickness or caliper C, measured in millimetres (mm), of the layer in which the adhesive is provided, typically onto at least a portion of the wearer facing surface of the article, and the viscous modulus $G''_{25}$ at about 100 rad/sec of the adhesive, is relevant to the scope of providing an easy and painless removal from the wearer's skin of such a adhesive applied on at least a portion of the wearer facing surface of an absorbent article for attachment of said article to the skin of a wearer.

The adhesive of the present invention is thus preferably provided as a layer having a thickness C such that the viscous modulus $G''_{25}$ (100 rad/sec) and the thickness C preferably satisfy the following empirical equation:

$$G''_{25} \leq [(7.00+C) \times 3000] Pa$$

and preferably also the following empirical equation:

$$G''_{25} \leq [(5.50+C) \times 1700] Pa$$

DETAILED DESCRIPTION OF THE INVENTION

According to the present invention the adhesive can be utilised on disposable absorbent articles such as diapers, sanitary napkins, panty liners, incontinence devices, perspiration pads and tampons. The word "skin" according to the present invention does not only relate to the specific derma of the user but includes the mucous tissue as well as the hair which is typically found in the genital region.

The skin of the wearer to which the articles are typically applied will vary considerably from person to person. In particular the type and amount of grease or sebum produced can vary considerably from person to person. Moreover, the wearers of such articles typically will apply creams to the area of skin which will contact the adhesives. These creams may be of a purely cosmetic nature i.e. moisturing creams or may be creams used to treat certain skin conditions by which the wearer may be afflicted ranging from mild skin irritation, and diaper rash to haemorrhoids and other more serious skin afflictions. In the latter case the use of such creams plays an essential role in the treatment of wearer's condition and cannot be relinquished. It is thus important to provide an adhesive which adheres to greasy skin. Accordingly the present invention provides an adhesive having a dry initial peel strength ($P_{DI}$) and a greasy initial peel strength ($P_{GI}$) as determined by the test method described herein, where the ratio $P_{DI}$ to $P_{GI}$ is from 1:1 to 1.0:0.2, preferably from 1:1 to 1:0.3. Typically for utilisation for disposable absorbent articles the dry initial peel strength is ($P_{DI}$) is from 0.1N/cm to 7.0N/cm, preferably from 0.1N/cm to 5.0N/cm, more preferably from 0.5N/cm to 3N/cm. The value of the grease initial peel strength is preferably the same as for the dry initial peel strength. However typically a lower level is achieved and is acceptable at levels from 0.1N/cm to 5N/cm, preferably from 0.1N/cm to 3N/cm, more preferably from 0.1N/cm to 2N/cm. It is also preferable of the adhesion to greasy skin is maintained over a period of wear time such that the ratio between the greasy initial peel strength ($P_{GI}$) and the greasy final peel strength ($P_{GF}$) is from 1:1 to 1:0.25 preferably from 1:1 to 1:0.5.

Due to the nature and environment in which such disposable absorbent articles are utilised it is also preferably a feature that the adhesive has a water absorption capacity as defined in the test herein of at least 3% by weight of said adhesive (so that the adhesive adheres directly onto wet or moist skin). In addition, it is also preferable that the adhesive maintains its adhesive strength in the presence of excess liquid for example when the wearer of the article urinates. In particular, the ratio of the peel strength of the adhesive as determined in the test methods herein should most preferably be maintained at a constant value such that the ratio of initial peel strength ($P_{DI}$) and the final peel strength ($P_{WF}$) is from 2:1 to 1:4, preferably from 2:1.25 to 2:4, most preferably from 2.0:1.5 to 2.0:2.5. Typically for disposable absorbent articles the initial peel strength for dry and more preferably also for wet skin should be from 0.1N/cm to 7.0N/cm, 0.1N/cm to 5.0N/cm, preferably from 0.5N/cm to 3.0N/cm.

It is further also preferable that the adhesive in addition to maintaining its peel strength over a period of time even in the presence of water also absorbs less than 15%, preferably less than 10%, more preferably less than 7% water. Whilst not intending to being bound by theory, it is believed that in order to obtain direct adhesion onto wet skin and maintain constant adhesion performance over a period of wear, even when exposed to excess liquids or high humidity the ability of the adhesive to absorb water needs to be considered. In particular, it has been identified that, not only the absolute ability of the adhesive needs to be considered, but also the rate of water absorption in order to provide an adhesive meeting the above identified performance parameters.

For example hydrocolloid particle containing adhesives which are known in the art comprising a 3-dimensional rubber matrix and colloidal absorbent particles dispersed therein are only able to absorb limited amounts of water through the colloidal particles themselves and not the matrix itself. In addition the rate at which water is absorbent is slow. Hence these prior art adhesives do not adhere to wet surfaces.

Prior art hydrogel adhesives on the other hand are able to not only absorb large quantities of water but also at a very fast rate. As a result such adhesives may be able to adhere, to wet surfaces, however due to the combination of fast rate of absorption and large absolute water uptake, these adhesives loose their adhesive strength rapidly in the presence of excess water or high humidity.

Accordingly the adhesives of the present invention exhibit both an ability to adhere directly to wet skin, by having a minimum absolute water absorption ability in combination with a rate of absorption such that the peel strength remains within defined levels over the period of wear.

The adhesive is provided with the preferred pattern, typically on the wearer facing surface of the article, as a layer having a thickness or calliper C that is preferably constant. The layer can be preferably continuous or alternatively discontinuous, e.g. in form of dots, spirals, or stripes.

Even though adhesives are used like pressure sensitive adhesives on human skin hair and mucous tissues, it is understood that the adhesive compositions could only with difficulty be considered typical pressure sensitive adhesives (referred to as PSA hereinafter) on the basis of the most characteristic theological behaviours identifying such materials.

In fact as the person skilled in the art of adhesives knows, the most characteristic feature that distinguishes a PSA from other substances that can temporarily adhere objects (e.g. water between two glass plates could) is the fact that their rheological parameters and especially the Elastic Modulus G' vary greatly with the frequency of applied stresses. More in particular, G' of PSA can increase over some orders of magnitude, while the frequency of applied stresses varies from typical bonding frequency to typical debonding frequency, i.e. 1 rad/s to 100 rad/s as indicated below.

As a first consequence, it is therefore inadmissible to define materials intended for use as "adhesives" by giving values of rheological parameters and especially of G' at a fixed value of frequency. This can be misleading because in the absence of other characteristics such as surface chemistry it will include materials which have no practical value. It is hence necessary that rheological characterisation must be on the basis of dynamic considerations. This not only applies to the Elastic Modulus G' but also to the viscous modulus G" and hence also for tan (d)=G"/G'.

It is well known that typical PSAs have not only a high variation of G' across the considered frequencies, but also that there is an even higher variation of G" which can get close or become even higher than the value of G', i.e. tan (d) becomes about or even greater than 1, in particular at the frequencies that are typical of debonding.

Without wishing to be bound by theory this can be interpreted as meaning that a high fraction of the energy applied for the debonding is dissipated within the adhesive (so it is not effective in causing the debonding) and through the interface of the adhesive and the skin, while this fact causes macroscopically the recording of a very high level of adhesive force.

As indicated above materials useful as adhesives according to the present invention have rheological characteristics which are measured at a reference temperature of 37° C. (as usual body temperature of humans) and in a range of frequencies. It has been found that upon application of an absorbent article with a adhesive the adhesive contact is formed at a low frequency, while debonding happens at the speed of removing the article. This speed is expressed as a frequency of 100 rad/s, while the low frequency of forming the adhesive bond has been found to be on the order of 1 rad/s. Therefore, the frequency range for use according to the present invention is between 1 and 100 rad/s.

In order to provide good conditions of bonding, i.e. at a frequency of about 1 rad/sec, the absolute values of the elastic modulus should not be too high, otherwise the adhesive is too hard and it is not able to intimately join or mold to the surface to which it is expected to adhere. It is also important to have a low absolute value of G" in order to have good cohesion while the material remains soft and capable of gently adhering to skin.

The ratio of $G'_{37}$ (1 rad/sec) over $G''_{37}$ (1 rad/sec) is important to ensure that these two values are balanced upon adhesion to the skin.

Importantly, the ratio of $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

needs to be large enough to ensure that the dynamic behaviour of both the elastic and the viscous module are maintained in a relationship which provides secure adhesion and painless and easy removal.

Finally the person skilled in the art will also recognise that the Glass Transition Temperature Tg of the adhesive composition, the specific heat capacity, and the specific heat conductivity are parameters which are useful to more fully define the group of useful adhesives.

The following set of characteristics should preferably be satisfied for the adhesive of the present invention:

| | |
|---|---|
| $G_{37}'$ (1 rad/sec) | is in the range 500 Pa to 20000 Pa, preferably 700 Pa to 15000 Pa, most preferably 1000 Pa to 10000 Pa. |
| $G_{37}''$ (1 rad/sec) | is in the range 100 Pa to 15000 Pa, preferably 100 Pa to 10000 Pa, most preferably 300 Pa to 5000 Pa. |
| the ratio of $G_{37}'$ (1 rad/sec)/ $G_{37}''$ (1 rad/sec) | is in the range of 1 to 30. |
| the ratio $\frac{G'_{37}(100 \text{ rad/sec}) - G''_{37}(100 \text{ rad/sec})}{G'_{37}(1 \text{ rad/sec}) - G''_{37}(1 \text{ rad/sec})}$ | is not less than 0.5, preferably in the range 0.7 to 3, most preferably in the range 1 to 1.8. |

The value of the ratio of $G'_{37}/G''_{37}$ at least for the frequency range above 1 rads/up to 100 rads/s should preferably be not less than 0.5, preferably from 0.7 to 10 and most preferably from 1 to 7.

The rheological behaviour can also be related to the values of the Glass Transition Temperature Tg. For topical adhesives according to the present invention Tg should preferably be less than 0° C., more preferably less than −5° C. and most preferably less than −10.

In order to provide adhesive compositions which satisfy the requirements of the above rheological and physical characteristics of an adhesive any medically suitable substantially water insoluble pressure sensitive adhesives comprising a polymer which forms a 3-dimensional matrix meeting the these characteristics may be utilised.

According to the present invention, the 3 dimensional matrix, also referred to herein as a gel, comprises as an essential component, a polymer, which can be physically, or chemically, cross-linked. The polymer may be naturally or synthetically derived. The uncrosslinked polymer includes repeating units or monomers derived from vinyl alcohols, vinyl ethers and their copolymers, carboxy vinyl monomer, vinyl ester monomers, esters of carboxy vinyl monomers, vinyl amide monomers, hydroxy vinyl monomers, cationic vinyl monomers containing amines or quaternary groups, N-vinyl lactam monomer, polyethylene oxides, polyvinylpyrrolidone (PVP), polyurethanes, acrylics such as methyl acrylate, 2-hydroxyethyl methacrylate, methoxydiethoxyethyl methacrylate and hydroxydiethoxyethyl methacrylate, acrylamides,and sulphonated polymers such as acrylamide sulphonated polymers for example 2-acrylamido methylpropane sulphonic acid, (acrylic 3-sulphopropyl ester) acid, salts thereof, and mixtures thereof. Also acrylonitrile, methacrylamide, N,N,- dimethylacrylamide, acrylic esters such as methyl, ethyl and butyl acrylates. Alternatively, the uncrosslinked polymer may be a homopolymer or copolymer of a polyvinyl ether, or a copolymer derived from a half ester of maleic ester. Similarly, any other compatible polymer monomer units may be used as copolymers such as, for example, polyvinyl alcohol and polyacrylic acid or ethylene and vinyl acetate.

As another alternative, the polymers may be block copolymer thermoplastic elastomers such as ABA block copolymers such as styrene-olefin-styrene block copolymers or ethylene-propylene block copolymers. More preferably such polymers include hydrogenated grade styrol/ethylene-butylene/styrol (SEBS), styrene/isoprene/styrene (SIS), and styrol/ethylene-propylene/styrol (SEPS).

Particularly preferred polymers are acrylics, sulphonated polymers such as acrylamide sulphonated polymers, vinyl alcohols, vinyl pyrrolidone, polyethylene oxide and mixtures thereof. Most preferred are nitrogen containing polymers.

According to the present invention the 3 dimensional adhesive matrix also essentially comprises a plasticiser, which is preferably a liquid at room temperature. This material is selected such that the polymer may be solubilized or dispersed within the plasticiser. For embodiments wherein irradiation cross linking is to be carried out, the plasticiser must also be irradiation cross linking compatible such that it does not inhibit the irradiation cross linking process of the polymer. The plasticiser may be hydrophilic or hydrophobic.

Suitable plasticisers include water, alcohols, polyhydric alcohols such as glycerol and sorbitol, and glycols and ether glycols such as mono- or diethers of polyalkylene gylcol, mono- or diester polyalkylene glycols, polyethylene glycols (typically up to a molecular weight of about 600), glycolates, glycerol, sorbitan esters, esters of citric and tartaric acid, imidazoline derived amphoteric surfactants, lactams, amides, polyamides, quaternary ammonium compounds, esters such phthalates, adipates, stearates, palmitates, sebacates, or myristates, and combinations thereof. Particularly preferred are polyhydric alcohols, polyethylene glycol (with a molecular weight up to about 600), glycerol, sorbitol, water and mixtures thereof.

Typically the adhesive comprises a ratio of polymer to plasticiser by weight of from 1:100 to 100:1, more preferably from 50:1 to 1:50. However, the exact amounts and ratios of the polymer and plasticiser will depend to a large extent on the exact nature of polymer and plasticisers utilised and can be readily selected by the skilled person in the art. For example a high molecular weight polymer material will require a greater amount of plasticiser than a low molecular weight polymer.

In addition, the adhesive also further preferably comprises a lipid-micellising polymer, i.e. a so-called hypercoiling polymer. This polymer functions to micellise and remove the rolled up pockets of grease from the gel-skin interface.

This hypercoiling polymer has the capability of more effectively solvating the primary surfactant micelles that contact hydrophobic skin contaminant such as skin lipid or skin creme. The consequence of this functional role is that the work of adhesion between adhesive and skin is progressively less affected by the presence of either or both surfactant or hydrophobic skin contaminant.

The hypercoiling polymer preferably comprises any of the following, either alone or in combination: poly (maleic acid styrene), poly (maleic acid butyl vinyl ether), poly (maleic acid propyl vinyl ether), poly (maleic acid ethyl vinyl ether) and poly (acrylic acid ethyl acrylate).

A particularly preferred example is an alternating copolymer of styrene and maleic anhydride. As discussed herein after the adhesive seeks to provide a biphasic structure on polymerisation. These two phases are hydrophilic and hydrophobic. The hydrophobic phase may be provided by a hydrophobic monomer which is initially maintained as part of the homogenous reaction mixture by way of a reactive solvent bridge. Alternatively and/or additionally the hydrophobic component is provided as a polymer which separates from the aqueous phase on polymerisation.

The exact amounts and ratios of the hypercoiling polymer will depend to a large extent on the nature of the components.

In certain circumstances the reaction mixture preferably comprises from 3% to 20%, and more preferably from 8% to 18% by weight of the reaction mixture, of a stabilised polymer dispersion that is used to provide a stable phase separated system. The polymer preferably comprises any of the following either alone or in combination: vinylacetate dioctyl maleate copolymer or ethylene-vinyl acetate copolymer. Ethylene-vinylacetate copolymer is preferred, such as that marketed under the trade name DM137 by Harlow Chemicals.

The adhesive also preferably comprise surfactants such as nonionic, cationic, anionic, amphoteric and any mixtures thereof.

Suitable nonreactive nonionic surfactants include but are not limited to those selected from the group consisting of the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles and most preferably about 5 to about 20 moles of ethylene oxide. Examples of such nonionic ethoxylated fatty alcohol surfactants are the Tergitol.™. 15-S series from Union. Carbide and Brij.™. surfactants from ICI. Tergitol.™. 15-S Surfactants include C.sub.11–C.sub.15 secondary alcohol polyethyleneglycol ethers. Brij.™ 58 Surfactant is Polyoxyethylene(20) cetyl ether, and Brij.™.76 Surfactant is Polyoxyethylene(10) stearyl ether.

Other suitable nonreactive nonionic surfactants include but are not limited to those selected from the group consisting of the polyethylene oxide condensates of one mole of alkyl phenol containing from about 6 to 12 carbon atoms in a straight or branched chain configuration, with about 3 to about 100 moles of ethylene oxide. Examples of nonionic surfactants are the Igepal.™.CO and CA series from Rhone-Poulenc. Igepal.™.CO surfactants include nonylphenoxy poly(ethyleneoxy) ethanols. Igepal.™. CA surfactants include octylphenoxy poly(ethyloneoxy) ethanols.

Another group of usable nonreactive nonionic surfactants include but are not limited to those selected from the group consisting of block copolymers of ethylene oxide and propylene oxide or butylene oxide.

Examples of such nonionic block copolymer surfactants are the Pluronic.™. and Tetronic ™. series of surfactants from BASF. Pluronic.™. surfactants include ethylene oxide-propylene oxide block copolymers. Tetronic.™. surfactants include ethylene oxide-propylene oxide block copolymers. Suitable examples are Pluronic L68 and Tetronic 1307. Particularly suitable examples are Pluronic L64 and Tetronic 1107.

Still other satisfactory nonreactive nonionic surfactants include but are not limited to those selected from the group consisting of sorbitan fatty acid esters, polyoxyethylene sorbitan fatty acid esters and polyoxyethylene stearates. Examples of such fatty acid ester nonionic surfactants are the Span.™., Tween.™., and Myrj.™. surfactants from ICI. Span.™. surfactants include $C_{12}$–$C_{18}$ sorbitan monoesters. Tween.™. surfactants include poly(ethylene oxide) $C_{12}$–$C_{18}$ sorbitan monoesters. Myrj.™. surfactants include poly(ethylene oxide) stearates.

Suitable anionic surfactants will normally include a hydrophobic moiety selected from the group consisting of (about $C_6$ to about $C_{20}$) alkyl, alkylaryl, and alkenyl groups and an anionic group selected from the group consisting of sulfate, sulfonate, phophate, polyoxyethylene sulfate, polyoxyethylene sulfonate, polyoxyethylene phosphate and the alkali metal salts, ammonium salts, and tertiary amino salts of such anionic groups.

Anionic surfactants which can be used in the present invention include but are not limited to those selected from the group consisting of (about $C_6$ to about $C_{20}$) alkyl or alkylaryl sulfates or sulfonates such as sodium lauryl sulfate (commercially available as Polystep.™ B-3 from Srepan Co.) and sodium dodecyl benzene sulfonate, (commercially available as Siponate.™.DS-10 from Rhone-Poulene); polyoxyethylene (about $C_6$ to about $C_{20}$) alkyl or alkylphenol ether sulfates with the ethylene oxide repeating unit in the surfactant below about 30 units, preferably below about 20 units, most preferably below about 15 units, such as Polystep.™.B-1 commercially available from Stepan Co. and Alipal.™.EP110 and 115 from Rhone-Poulenc; (about $C_6$ to about $C_{20}$) alkyl or alkylphenoxy poly(ethyleneoxy)ethyl mono-esters and di-esters of phosphoric acid and its salts, with the ethylene oxide repeating unit in the surfactant below about 30 units, preferably below about 20 units, most preferably below about 15 units, such as Gafac.™.RE-510 and Gafac.™.RE-610 from GAF.

Cationic surfactants useful in the present invention include but are not limited to those selected from the group consisting of quaternary ammonium salts in which at least one higher molecular weight group and two or three lower molecular weight groups are linked to a common nitrogen atom to produce a cation, and wherein the electrically-balancing anion is selected from the group consisting of a halide (bromide, chloride, etc.), acetate, nitrite, and lower alkosulfate (methosulfate etc.). The higher molecular weight substituent(s) on the nitrogen is/are often (a) higher alkyl group(s), containing about 10 to about 20 carbon atoms, and the lower molecular weight substituents may be lower alkyl of about 1 to about 4 carbon atoms, such as methyl or ethyl, which may be substituted, as with hydroxy, in some instances. One ore more of the substituents may include an aryl moiety or may be replaced by an aryl, such as benzyl or phenyl.

In a particularly preferred embodiment of the invention the surfactant comprises at least one propylene oxide/ethylene oxide block copolymer, for example such as that supplied by BASF Plc under the trade name Pluronic L64. The reaction mixture ideally comprises form 0.1% to 5%, by weight of the reaction mixture, of surfactant.

The surfactant acts to remove the grease from the skin and to form the removed grease into isolated pockets within the hydrogel without reducing the work of adhesion of the coating.

Other common additives known in the art such as preservatives, antioxidants, pigments, mineral fillers and mixtures thereof may also be comprised within the adhesive composition in quantities up to 10% by weight each respectively.

According to the present invention the polymer component of the adhesive can be physically or chemically cross linked in order to form the 3 dimensional matrix. Physical cross linking refers to polymers having cross links which are not chemical covalent bonds but are of a physical nature such that there are areas in the 3 dimensional matrix having high crystallinity or areas having a high glass transition temperature. Chemical cross-linking refers to polymers which are linked by chemical bonds. Preferably the polymer is chemically cross-linked by radiation techniques such as thermal-, E beam-, UV-, gamma or micro-wave radiation.

In addition when chemical crosslinks are formed in the system, a polyfunctional cross linker and/or a free radical initiator may be present in the premix to initiate the crosslinking upon irradiation. Such an initiator can be present in quantities up to 5% by weight, preferably from 0.02% to 2%, more preferably from 0.02% to 0.2%. Suitable photoinitiators include type I-α-hydroxy-betones and benzilidimethyl-betols e.g. Irgocure 651 which are believed to on irradiation to form benzoyl radicals that initiate polymerization. Particularly preferred is 1-hydroxycyclohexylphenylketone (available under the trade name Irgacure 184 from Ciba Speciality Chemicals). In addition from 0.02% to 2% of thermal initiators may also be used.

The resulting adhesive composition is mainly hydrophilic. Hydrophobic and mixed phase compositions are dependent upon the nature of the components of the adhesive. In addition a mixture of monomers whether hydrophilic or both hydrophilic and hydrophobic may result in a single phase or mixed phase of at least 2 phases. Preferably, the adhesives of the present invention are mixed phase hydrophilic hydrophobic.

A mixture of monomers which may result in 1, 2 or more phases are preferred. Mixed phase adhesives are compositions in which both hydrophobic and hydrophilic components, preferably in both plasticisers and polymers, form two or more separate phases. In such cases an emulsifier is preferably present at a suitable level to form stable emulsions between the incompatible phases.

Whilst not intending to be bound by theory it is believed that the improved peel strength liquid stability particularly with respect to water of the adhesives is obtained from a monomer mix comprising both hydrophilic e.g. polar and/or ionic monomers preferably an ionic water soluble monomer and hydrophobic i.e nonionic monomers. Preferably the ratio of hydrophilic monomers to hydrophobic monomers should be in the range of from 5:1 to 1:5, preferably from 3:1 to 1:3, more preferably from 2:1 to 1:2. The hydrophilicity and hydrophobicity of a monomer component is always relative to the other component. Typically prior art hydrogel adhesives comprise hydrophilic monomers only, as a consequence of which they have a high rate of water absorption and do not maintain adhesion after exposure to excess liquid. Whilst not intending to be bound by theory, it is believed that the presence of a hydrophobic component in the adhesive matrix reduces the rate of absorption of water of the adhesive. As a result the distribution of the water absorbed by the adhesive is more uniform. Consequently a water film is not generated between the surface of the skin and the adhesive, which if present, prevents the formation of bonds between skin and adhesive and thus the adhesive capacity of the adhesive itself.

Thus the invention seeks to provide a homogeneously dispersed reaction mixture comprising both hydrophobic and hydrophilic components which, on polymerisation separates into a biphasic or a multiphasic structure. The phases have in some cases been observed to have a thickness of about 100 microns +/−50 microns. The reaction mixture may contain one or more surface active agents which may assist or promote phase separation but in the course of polymersation become anistropically distributed between the result phases.

The presence of a hydrophobic monomer or polymer may be necessary in the initial homogenous dispersion in order to more effectively promote phase separation.

It is a consequence of this invention that the phase separated material contains relatively hydrophobic regions, which enable the polymer to function as a pressure sensitive adhesive, and substantially hydrophilic region, which enable the surface active agent to function in an aqueous environment at the interface between the polymer and mammalian skin. When the polymer is placed in contact with skin, the nature and quantity or surface active agent are chosen to bring about the removal of natural or synthetic hydrophobic material, such as skin lipid or skin creme, from the skin surface without adversely diminishing the work of adhesion between the hydrophobic domains and the skin surface. In as much as both the polymeric adhesive formed in this invention and the skin with which it is contacted are deformable under conditions of normal use, an equilibrium interfacial situation is reached in which some spatial exchange of hydrophobic regions and hydrophobic regions will have taken place on the skin surface.

Suitable preferred hydrophilic monomers are acrylic acid, and salts thereof, 2-acrylamido methylpropane sulphonic acid, acrylic (3-sulphopropyl) ester acid and salts thereof and combinations thereof. Suitable hydrophobic monomer components are acrylamide, acrylonitrile, methyl-, ethyl-, butyl hexyl, iso octyl- and isodecyl acrylates and methacrylate, vinyl ethers, vinyl pyrrolidine, gylcidyl acrylate and 2-hydroxyethyl acrylate, tehra-hydrofurfuryl acrylate, hydroxypropyl acrylate, vinyl propionate and vinyl butyrate, and combinations thereof. Particularly preferred are ethoxy ethyl acrylate or butyl acrylate.

When the adhesive comprises a hydrophobic component, such as butyl acrylate as well as a hydrophilic monomer (i.e. the aforesaid water soluble ionic monomer), such as NaAMPS, the nonionic water soluble monomer, for example NNDMA, acts as a so-called "reactive solvent bridge" to provide intimate mixing of the various seemingly incompatible components of the reaction mixture prior to polymerisation. The reaction mixture thus has a homogenous structure containing both hydrophilic and hydrophobic components that are intimately mixed, as the NNDMA acts as a solvent for both hydrophilic and hydrophobic materials, providing a clear compatible coating solution or dispersion. As the reactive solvent bridge is polymerised and thus essentially removed from the reaction mixture the stability of the system is adversely affected and the compatible coating solutions or dispersions undergo phase separation so as to provide a biphasic structure.

In preparing adhesive compositions in accordance with the invention, the ingredients will usually be mixed to provide a reaction mixture in the form of an initial pre-gel aqueous based liquid formulation, and this is then converted into a gel by a free radical polymerisation reaction. This may be achieved for example using conventional thermal initiators and/or photoinitiators or by ionizing radiation. Photoinitiation is a preferred method and will usually be applied by subjecting the pre-gel reaction mixture containing an appropriate photoinitiation agent to UV light after it has been spread or coated as a layer on siliconised release paper or other solid substrate. The incident UV intensity, at a wavelength in the range from 240 to 420 nm, is ideally substantially 40 mW/cm$^2$. The processing will generally be carried out in a controlled manner involving a precise predetermined sequence of mixing and thermal treatment or history.

The UV irradiation time scale should ideally be less than 60 seconds, and preferably less than 10 seconds to form a gel with better than 95% conversion of the monomers and for conversion better than 99.95% exposure to UV light less than 60 seconds and preferably less than 40 seconds is preferred. Those skilled in the art will appreciate that the extent of irradiation will be dependent on the thickness of the reaction mixture, concentration of photoinitiator and nature of substrate on to which the reaction mixture is coated and the source of UV.

These timings are for medium pressure mercury arc lamps as the source of UV operating at 100 W/cm. The intensity of UV @ 254 nm and 313 nm reaching the surface of the substrate is approximately 150 $\mu$W/cm$^2$ and 750 $\mu$W/cm$^2$. For a given lamp UV intensity in a function of the operating power and distance of the reaction mixture from the UV source.

In order to minimize and preferably eliminate the presence of any residual monomers it is important to ensure that the reaction is complete. This is dependent upon a number of factors such as the substrate onto which the adhesive is applied, the type and intensity of the ultra violet light and the number of ultra violet light passes. Preferably the conversion of the hydrophilic monomers present such as NaAMPS should be 98%, preferably 99% most preferably 99.9% so that the amount of monomer within the adhesive is 4600 microg/g or less, preferably 2300 microg/g or less, most preferably 230 microg/g or less. Similarly, the conversion of the hydrophobic monomers present such as NNDMA should be 99%, preferably 99.9%, most preferably 99.99% so that the amount of monomer present in the adhesive is 2200 microg/g or less, preferably 220 microg/g or less, more preferably 22 microg/g or less.

The adhesive is thus typically formed by polymerising an aqueous reaction comprising from 5 to 50%, preferably from 30% to 50% by weight of the reaction mixture, of hydrophilic monomer, i.e. an ionic water soluble monomer, from 10% to 50%, preferably from 15% to 45% by weight of the reaction mixture, of a plasticiser (other than water), from 10% to 50%, preferably from 15% to 30% more preferably from 15% to 25% by weight of the reaction mixture, of a hydrophobic nonionic monomer, i.e. nonionic water soluble monomer, from 3 to 40%, by weight of the reaction mixture, of water. If present the reaction mixture comprises from to 10%, by weight of the reaction mixture, of a surfactant. Similarly the reaction mixture may also comprise from 0.1% to 5%, by weight of the reaction mixture, of a lipid micelling polymer.

The adhesive is provided, typically on at least a portion of the wearer facing surface of the article, as a layer having a thickness or caliper C that is preferably constant, or that alternatively can vary over the surface of application of the adhesive.

When considering particularly the removal phase of an adhesive composition for attachment to the skin of a wearer, it is commonly recognised that good conditions of removal, i.e. at a frequency of about 100 rad/sec, of the adhesive applied to at least part of the wearer facing surface of the article, are achieved when the adhesive can be easily removed from the skin, and particularly from the bodily hair that may be located on this area of the skin, where the article contacts the body, without causing pain to the wearer, therefore without adhering too hard upon removal, to the skin and the hair of the wearer. Moreover, a good removal implies that the adhesive does not leave residues on the skin or on the hair.

The relationship between the thickness or caliper C measured in millimetres (mm) of the layer of the adhesive typically onto at least part of the wearer's facing surface of the article, and the viscous modulus $G''_{25}$ at 25° C. at about 100 rad/sec of the topical adhesive gives an indication of painless and easy removal of the adhesive from the skin.

Without being bound to any theory, it is believed that for higher values of $G''_{25}$ at 100 rad/sec, which overall correspond to a higher adhesiveness of the composition, a thicker calliper or thickness C of the adhesive layer is needed so that the energy applied for the removal is more evenly distributed within the mass of the adhesive, and is therefore transferred smoothly to the skin, so avoiding peaks of energy that typically cause the pain sensation to the wearer. In other words, thinner layers of the adhesive necessitate an adhesive with a lower $G''_{25}$ at 100 rad/sec to achieve a reduced pain sensation upon removal of the article.

According to the present invention, the adhesive is preferably provided as a layer having a thickness C such that the viscous modulus $G''_{25}$ (100 rad/sec) and the thickness C of the adhesive layer satisfy the following empirical equation:

$$G''_{25} \leq [(7.00+C) \times 3000] Pa$$

and preferably the following empirical equation:

$$G''_{25} \leq [(5.50+C) \times 1700] Pa$$

While in a preferred embodiment of the present invention the thickness C of the adhesive layer is constant, such an adhesive layer can also have different thicknesses in different portions of the wearer facing surface of the article where it is applied, provided that the above mentioned relationship between C and $G''_{25}$ is in any case satisfied in each portion.

Description of the Disposable Absorbent Article

Absorbent articles, in which the adhesive according to the present invention can be used, can be made by any of the ways usual in the art. The application of the adhesive to the wearer facing surface, typically the topsheet surface of an absorbent article should not cause major problems to those skilled in the art since it can be provided by any well known techniques commonly used to apply adhesives. Most preferably the adhesive is provided in a pattern of small incremental areas such as dots or similar.

The adhesive is applied on at least portion of the wearer facing surface of disposable absorbent articles in a layer having a thickness or caliper that is preferably constant, or that alternatively can vary over the surface interested by the application of the adhesive. The adhesive can be applied to the wearer facing surface of the article by any means known in the art such as slot coating, spiral or bead application or printing. Typically the adhesive is applied at a basis weight of from 20 g/m² to 2500 g/m², preferably from 500 g/m² to 2000 g/m², most preferably from 700 g/m² to 1500 g/m² depending in the end use envisioned.

If possible, the article also provides breathability by being at least water vapour permeable, preferably air permeable to prevent stuffiness. Breathability, if not supported by the adhesive as such, can be limited to the area of the article where no adhesive is applied.

The adhesive on an article is preferably protected prior to use. This protection can be provided by a release liner such as a siliconised or surfactant treated paper, providing easy release for the selected adhesive.

This invention can be used beneficially on disposable absorbent articles which are applied directly to the skin of a user. The article usually exhibits absorbency for bodily fluids, the protection of the user's garments from soiling, is comfortable to the user, and is easy to produce and to package. The disposable absorbent article is described below by reference to a diaper, a sanitary napkin or catamenial, however panty liners, adult incontinence articles, tampons or perspiration pads are also included under the term disposable absorbent articles. The term "sanitary napkin", as used herein, refers to an article which is worn by females adjacent to the pudendal region and which is intended to absorb and contain the various body fluids which are discharged from the body (e.g., vaginal discharges, menses, and/or urine) and which is intended to be discarded after a single use. A disposable absorbent article is preferably thin, more preferably between 1 and 5 mm thick and either substantially flat prior to use or in a preshaped form.

The terms "joined" or "affixed", as used herein, encompasses configurations whereby a first member is directly connected to a second member and configurations whereby a first member is indirectly connected to a second member by connecting the first member to intermediate members which in turn are connected to the second member.

The sanitary napkin has two main surfaces, a body contacting or wearer facing surface on which the adhesive is applied and a garment facing or contacting surface. In a one preferred embodiment a sanitary napkin of the present invention comprises a liquid pervious topsheet, a liquid. impervious backsheet joined to the topsheet, and an absorbent core intermediate the topsheet and the backsheet. In an alternative embodiment, the sanitary napkin or panty liner may utilize the adhesive to absorb quantities of liquid up to amounts of about 10 g, such that a separate core and topsheet are not required. Such products preferably have a backsheet as described below.

The topsheet is compliant, soft feeling, and non-irritating to the wearer's skin. The topsheet also can have elastic characteristics allowing it to be stretched in one or two directions in portions of the topsheet or throughout its extension. Further, the topsheet is fluid pervious permitting fluids (e.g., menses and/or urine) to readily penetrate through its thickness.

Preferred topsheets for use in the present invention are typically selected from high loft nonwoven topsheets and apertured formed film topsheets. Apertured formed films are especially preferred for the topsheets because they are pervious to body exudates and yet non absorbent and have a reduced tendency to allow fluids to pass back through and rewet the wearer's skin. Thus, the surface of the formed film that is in contact with the wearer remains dry, thereby reducing body soiling and creating a more comfortable feel for the wearer. Suitable formed films are described in U.S. Pat. No. 3,929,135; U.S. Pat. No. 4,324,246; U.S. Pat. No. 4,342,314; U.S. Pat. No. 4,463,045; and U.S. Pat. No. 5,006,394. Particularly preferred micro apertured formed film topsheets are disclosed in U.S. Pat. No. 4,609,518 and U.S. Pat. No. 4,629,643. A preferred topsheet for the present invention comprises the formed film described in one or more of the above patents and marketed on sanitary napkins by The Procter & Gamble Company of Cincinnati, Ohio as "DRI-WEAVE".

Adhesives are most suitably used on topsheets having not a homogeneous distribution of liquid passage ways but only a portion of the topsheet comprising liquid passage ways oriented such that they result in a centrally permeable and peripherally impermeable topsheet for liquids.

Another alternative are so called hybrid topsheets which incorporate fibrous and film like structures particularly useful embodiments of such hybrid topsheets are disclosed in PCT publications WO 93/09744; WO 93/11725 or WO 93/11726.

When referring to the topsheet a multi layer structure or a mono layer structure is contemplated. The hybrid topsheet mentioned above is such a multi layer design but other multi layer topsheets such as primary and secondary topsheet designs are also considered.

The absorbent core also can comprise multiple layers and provides fluid storage and distribution function.

Positioned in fluid communication with, and typically underlying the topsheet is the absorbent core. The core can comprise any usual absorbent material or combinations thereof. It preferably comprises absorbent gelling materials usually referred to as "hydrogel", "superabsorbent", "hydrocolloid" materials in combination with suitable carriers.

Suitable absorbent gelling materials for use herein will most often comprise a substantially water-insoluble, slightly cross-linked, partially neutralised, polymeric gelling material. This material forms a hydrogel upon contact with water. Such polymer materials can be prepared form polymerizable, unsaturated, acid-containing monomers, such as acrylic acid, which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins/panty liners.

An embodiment of the core, particularly useful in the application of the present invention, comprises a double layer tissue laminate formed by folding the tissue onto itself. These layers can be joined to each other. Absorbent gelling material or other optional material can be comprised between the layers.

The absorbent core can include optional components normally present in absorbent webs such as odor control agents, in particular suitable zeolites.

The backsheet primarily prevents the exudates absorbed and contained in the absorbent core from wetting articles that contact the absorbent product such as underpants, pants, pyjamas and undergarments. The backsheet is preferably impervious to liquids (e.g. menses and/or urine) and usually manufactured from a thin plastic film.

The backsheet typically extends across the whole of the absorbent core and can extend onto and form part of the topsheet by folding around the absorbent core. Thereby a topsheet configuration as disclosed in U.S. Pat. No. 4,342,314, column 16, lines 47–62 can be achieved without the requirement to selectively aperture the topsheet.

Preferably, the backsheet also provides breathability to the absorbent article by being at least water vapour permeable, preferably air permeable. The backsheet can be a laminate material e.g. of a combination of microporous film and/or non-woven material, and/or apertured formed film. Breathability if desired can be limited to the periphery or the center of the backsheet or it can be across the whole backsheet.

According to the present invention the adhesive as described herein may also find application to attach other articles to the skin. The adhesives may for example find utility to adhere functional articles which adhere to the skin such as cosmetic or pharmaceutical delivery articles which provide a substance to the skin such as skin treatment substances, cream, lotions, hormones, vitamins, deodorants, drugs; cosmetic or pharmaceutical delivery articles provide a substance to emanate away from the skin such as insecticides, inhalation drugs, perfumes and; functional articles which are not necessarily attached to the skin, but which require a high residence time on the skin such as decorative cosmetics, (lipstick, eye shadow, stage make-up) and cleaning articles (hand cleaners, face masks and hygienic pore cleansers). Such articles are preferably non-absorbent for bodily liquids.

The adhesive may also in addition find application to attach articles to the skin such as protective articles such as genital-, knee- or elbow-protectors or bandages; clothing such as bras, surgical gowns, or parts of garments during fitting at a tailor; nasal plasters; prosthesis such as breast replacements or wigs; cold wraps e.g. to provide pain relief from bruises and to reduce swelling; thermal wraps comprising thermal cells as disclosed for example in WO97/36968 and WO97/4936 1 to provide relief of temporary and chronic pain such as neck wraps as disclosed in for example U.S. Pat. No. 5,728,146, knee wraps exemplified in WO97/013 11, and back wraps as disclosed for example in U.S. Pat. No. 5,741,318; hearing aids; protective face masks (for the reduction or prevention of inhalation of noxious substances); ornamental articles such as jewelry, earrings, guises, tattoos; goggles or other eye wear; ostomy devices, tapes, bandages, dressings of general utility, wound healing and wound management devices; and biomedical skin electrodes such as ECG, EMG, EEG, TENS electrosurgery, defibrillation, EMS and electrodes for facial/beauty applications; and fixation products and/or devices intended to affix patient catheters, tubing leadwires cables etc.

Test Methods
Peel Adhesion Method

This is a quantitative method to determine the average peel force required to remove a skin at a specified peel angle and speed.

| Equipment | |
|---|---|
| Scissors | Convenient source |
| Standard ruler | Convenient source |
| Steel Roller | 5.0 kg Mass. 13 cm in diameter and 4.5 cm in width covered with 0.5 mm thick rubber. |
| Polyester Film | PET 23μ available from EFFEGIDI S.p.A., 43052 Colorno, Italy. |
| Transfer Adhesive | 3M 1524 available from 3M Italia S.p.a., 20090 Segrate Italy |
| Stop watch | Convenient source |
| Tensile Tester | Instron mod.: 6021(or equivalent) |

| Test procedure | |
|---|---|
| A) Tensile Tester Peel Settings: | |
| Load cell | 10N |
| Test Speed | 1000 mm/min |
| Clamp to Clamp distance | 25 mm |
| Pre Loading | 0.2N |
| Test Path "LM" | 50 mm |
| Measure variable | F average (N) in "LM" |

B) Skin Condition and Preparation

The sample is peel from the forearm. There are 3 conditions of the skin that are tested:

1) Dry: The forearm is untreated and not wiped prior to test or between repetitions.

2) Wet: To one cotton disk (Demak'up diameter 5.5 cm, weight about 0.6 g), 3 ml of distilled water is added. Next the disk is then wiped with a light pressure 3 times over the test area on the forearm. (The test area of the forearm is a rectangle approximately 2 cm wider and longer than the adhesive area).

3) Greasy: To one cotton disk (Demak'up diameter 5.5 cm, weight about 0.6 g), 4 drops (about 0.2 g) of 'Nivea Body' are added. The disk is then folded in on itself to ensure the cream is absorbed. Next the disk is then wiped with a light pressure 3 times over the test area on the forearm. (The test area of the forearm is a rectangle approximately 2 cm wider and longer than the adhesive area).

C) Sample Preparation

1. Allow the samples to adjust to conditioned room (23±2° Celsius and 5±2% RH) for about 1 hr.

2. Prepare rectangular adhesive samples 260 mm±2 length and 20 mm±2 wide.

3. Attach on the sample surface the polyester film (using the transfer adhesive to attach the polyester to the substrate surface).

4. Each test specimen should be prepared individually and tested immediately.

5. Remove the release paper from the adhesive without touching it. Attach one end to the skin (see section B).

6. Roll the Steel Roller for 160 mm along the adhesive strip, once in each direction.

D) Test Environment

There are 2 environments the adhesive can be tested in:

1) Conditioned Room as described in C1.

2) Wet Environment. Here, after step C4, the specimen is taken and put in a humidity controlled oven for 3 hours at 85 degC. It is then taken out and steps C5, C6 are carried out.

E) Execution 1 minute after Step C6, take the free end of the specimen (approx. 100 mm long) and insert it in the upper end of the adhesion testing machine. Ensure the specimen is at a 90 degree angle to the forearm. Start the testing machine.

F) Report

Report the average of the peel strength of 5 tests. The single values are the base to calculate the standard deviation between the samples.

Residual Monomer Test Method

Test Sample 1 gram of a hydrogel sample is taken and emersed in 100 ml 0.9% saline water.

The sample is left in the saline at 40 degC. for 24 hours.

An aliquot of the liquid is diluted and analysed by electrospray LC/MS/MS.

Calibration Sample 1 gram of reference monomers (eg NaMPS) are dissolved in 100 ml 0.9% saline water.

An aliquot of the liquid is diluted and analysed by electrospray LC/MS/MS.

Evaluation

The concentration of the test and calibration sample are determined by linear regression analysis using a software package such as VG Mass Lynx.

EXAMPLES

All formulations detailed below were coated onto polyurethane foam (EV1700X from Caligen) at a coat weight of 0.8 to 1.6 kg per square meter and cured by exposure to ultraviolet radiation emitted from a medium pressure mercury arc lamp operating at 100 W/cm power for 10 seconds.

Example 1

Mix 6.0 g of Irgacure 184 with 20 g IRR280 (PEG400 diacrylate) from UCB (Solution A). To 0.07 g of Irgacure 184 add 23.5 g of NNDMA and stir for one hour (keep container covered from light). Add 30 g of glycerol to this and stir for 5 minutes, followed by 40 g of NaAMPS (58%). Stir for another 5 minutes. Add 0.13 g of Solution A and stir the whole formulation for 1 hour before use.

Example 2

Mix 6.0 g of Irgacure 184 with 20 g IRR280 (PEG400 diacrylate) from UCB (Solution A). To 0.07 g of Irgacure 184 add 23.5 g of NNDMA and stir for one hour (keep container covered from light). Add to this 10 g of Mowilith DM137 (50% dispersion of ethylene vinyl acetate copolymer in water from Harco) and stir for 5 minutes. Add 30 g of glycerol to this and stir for 5 minutes, followed by 40 g of NaAMPS (58%). Stir for another 5 minutes. Add 0.13 g of Solution A and stir the whole formulation for 1 hour before use.

Example 3

Mix 6.0 g of Irgacure 184 with 20 g IRR280 (PEG400 diacrylate) from UCB (Solution A). To 0.07 g of Irgacure 184 and 23.5 g of NNDMA and stir for one hour (keep container covered from light). Add to this 10 g of Mowilith DM137 (50% dispersion of ethylene vinyl acetate copolymer in water from Harco) and stir for 5 minutes. Add 30 g of glycerol to this and stir for 5 minutes, followed by 40 g of NaAMPS (58%). Stir for another 5 minutes. Add 0.5 g of Pluronic L64 (poly(ethylene glycol)-block-poly(propylene glycol)-block-poly(ethylene glycol) available from BASF). Add 0.13 g of Solution A and stir the whole formulation for 1 hour before use.

Example 4

Mix 6.0 g of Irgacure 184 with 20 g 1RR280 (PEG400 diacrylate) from UCB (Solution A). To 0.07 g of Irgacure 184 add 23.4 g of NNDMA and stir for one hour (keep container covered from light). Add to this 2 g of Mowilith DM137 (50% dispersion of ethylene vinyl acetate copolymer in water from Harco) and stir for 5 minutes. Add 36 g of glycerol to this and stir for 5 minutes, followed by 40.36 g of NaAMPS (58%). Stir for another five minutes. Add 0.25 g of Pluronic L64 (poly(ethylene glycol)-block-poly (propylene glycol)-block-poly(ethylene glycol) available from BASF). To this add 0.8 g of a 30% aqueous solution of poly(styrene-alt-maleic acid) sodium salt available from Aldrich and stir for 10 minutes. Add 0.13 g of Solution A and stir the whole formulation for 1 hour before use.

Example 5

Mix 6.0 g of Irgacure 184 with 20 g IRR280 (PEG400 diacrylate) from UCB (Solution A). To 0.07 g of Irgacure 184 add 23.4 g of NNDMA and stir for one hour (keep container covered from light). Add to this 10 g of Mowilith DM137 (50% dispersion of ethylene vinyl acetate copolymer in water from Harco) and stir for 5 minutes. Add 36 g of glycerol to this and stir for 5 minutes, followed by 40.36 g of NaAMPS (58%). Stir for another 5 minutes. Add 0.25 g of Pluronic L64 (poly(ethylene glycol)-block-poly (propylene glycol)-block-poly(ethylene glycol) available from BASF). To this add 0.8 g of a 30% aqueous solution of poly(styrene-alt-maleic acid) sodium salt available form Aldrich and stir for 10 minutes. Add 0.13 g of Solution A and stir the whole formulation for 1 hour before use.

Example 6

Mix 6.0 g of Irgacure 184 with20 g IR280 (PEG400 diacrylate) from UCB (Solution A). To 0.07 g of Irgacure 184 add 23.4 g of NNDMA and stir for one hour (keep container covered from light). Add to this 10 g of Mowilith DM137 (50% dispersion of ethylene vinyl acetate copolymer in water from Harco) and stir for 5 minutes. Add 36 g of glycerol to this and stir for 5 minutes, followed by 40.36 g of NaAMPS (58%). Stir for another 5 minutes. Add 0.5 g of Pluronic L64 (poly(ethylene glycol)-block-poly (propylene glycol)-block-poly(ethylene glycol) available from ASF). To this add 0.8 g of a 30% aqueous solution of poly(styrene-alt-maleic acid) sodium salt available from Aldrich and stir for 10 minutes. Add 0.13 g of Solution A and stir the whole formulation for 1 hour before use.

Example 7

Mix 6.0 g of Irgacure 184 with 20 g IRR280 (PEG400 diacrylate) from UCB (Solution A). To 0.07 g of Irgacure 184 add 23.4 g of NNDMA and stir for one hour (keep container covered from light). Add to this 20 g of Mowilith DM137 (50% dispersion of ethylene vinyl acetate copolymer in water from Harco) and stir for 5 minutes. Add 36 g of glycerol to this and stir for 5 minutes, followed by 40.36 g of NaAMPS (50%). Stir for another 5 minutes. Add 0.5 of Pluronic L64 (poly(ethylene glycol)-block-poly(propylene glycol)-block-poly(ethylene glycol) available from BASF). To this add 0.8 g of a 30% aqueous solution of poly(styrene-alt-maleic acid) sodium salt available from Aldrich and stir for 10 minutes. Add 0.13 g of Solution A and stir the whole formulation for 1 our before use.

Example 8

To parts glycerol, were added 40.4 parts of a 58% solution of the sodium salt of 2-acrylamido-2-methylpropane sulphonic acid (NaAMPS) (LZ2405A) together with 0.5 parts Pluronic LF64 (BASF), and the solution stirred to ensure uniform mixing. To the solution was added 0.13 parts of solution containing 20 parts of polyethylene glycol diacrylate (PEG600) (product of UCB Chemicals marketed under the trade name designation of Ebacryl 11) in which 6 parts of 1-hydroxycyclohexyl phenyl ketone (product of Ciba and marketed under the trade name designation of Irgacure 184) had been dissolved. A promised solution of 8 parts butyl acrylate and 15.7 parts N,N-dimethylacrylamide (Kohjin) was added to that reaction mixture and this final solution cured by exposure to UV light as in example 1. Optical phase contrast microscopy showed that resultant gel to have a regularly phase-segregated surface and enhanced adhesion to skin that had previously treated with skin cream (Nivea).

| | Results | | | | | |
|---|---|---|---|---|---|---|
| | Subject 1 | | | Subject 2 | | |
| Example | Dry ($P_{DI}$) | Greasy ($P_{GI}$) 1 min | 10 min | Dry ($P_{DI}$) | Greasy ($P_{GI}$) 1 min | 10 min |
| 1 | 1.75 | 0.13 | — | 1.57 | 0.19 | — |
| 2 | 2.96 | 0.16 | — | 3.18 | 0.44 | — |
| 3 | 2.81 | 0.52 | 0.33 | 2.46 | 0.67 | 0.61 |
| 4 | 0.81 | 0.15 | 0.26 | 0.96 | 0.29 | 0.47 |
| 5 | 1.2 | 0.52 | 0.69 | 2.2 | 0.83 | 0.88 |
| 6 | 1.6 | 0.45 | 0.6 | 2.2 | 0.64 | 0.56 |
| 7 | 1.2 | 0.49 | 0.62 | 1.6 | 0.74 | 0.88 |

What we claim is:

1. An adhesive for a topsheet of a disposable absorbent article having a wearing facing surface and a garment facing surface opposed thereto;

said adhesive covering at least a portion of said wearing facing surface;

wherein said adhesive has dry peel strength ($P_{DI}$) and a greasy peel strength ($P_{GI}$);

wherein the ratio of $P_{DI}$ to $P_{GI}$ ranges from 1:1 to 1:0.2;

wherein said adhesive is a substantially water-insoluble, pressure sensitive, mixed phase adhesive comprising a polymer that forms a three-dimensional matrix;

wherein said polymer comprises a hydrophilic component and a hydrophobic component;

wherein the ratio of said hydrophilic component to said hydrophobic component is from 5:1 to 1:5; and, wherein said polymer is formed into a gel by free radical polymerization.

2. The adhesive of claim 1, wherein the ratio of said dry peel strength ($P_{DI}$) to said greasy peel strength ($P_{GI}$) ranges from 1:1 to 1:0.3.

3. The adhesive of claim 1, wherein said dry peel strength ($P_{DI}$) of said adhesive ranges from 0.1 N/cm to 5.0 N/cm.

4. The adhesive of claim 3, wherein said dry peel strength ($P_{DI}$) of said adhesive ranges from 0.5 N/cm to 3.0 N/cm.

5. The adhesive of claim 1, wherein said greasy peel strength ($P_{GI}$) of said adhesive ranges from 0.1 N/cm to 5.0 N/cm.

6. The adhesive of claim 1, wherein said adhesive is provided as a layer having a thickness, C, in millimeters;

wherein said adhesive has a viscous modulus at a temperature of 25° C. ($G''_{25}$(100 rad/sec)); and, wherein said viscous modulus ($G''_{25}$(100 rad/sec)) is defined by the equation:

$$G''_{25} \leq [(7.00+C) \times 3000] \text{Pa}.$$

7. The adhesive of claim 1, wherein said adhesive has an elastic modulus at a temperature of 37° C. ($G'_{37}$(1 rad/sec)), and a viscous modulus at a temperature of 37° C. ($G''_{37}$ (1 rad/sec));

wherein $G'_{37}$ (1 rad/sec) ranges from 500 Pa to 20000 Pa;

wherein $G''_{37}$ (1 rad/sec) ranges from 100 Pa to 15000 Pa; and, wherein the ratio $G'_{37}$ (1 rad/sec)/$G''_{37}$ (1 rad/sec) ranges from 1 to 30.

8. The adhesive of claim 7, wherein $G'_{37}$ (1 rad/sec) ranges from 700 Pa to 15000 Pa; and, wherein $G''_{37}$ (1 rad/sec) ranges from 100 Pa to 10000 Pa.

9. The adhesive of claim 1, wherein said adhesive comprises:
   a polymer selected from the group consisting of polymers of acrylics, vinyl alcohols, and vinyl pyrrolidine, sulphonated polymers, polyethylene oxide, copolymers thereof, and mixtures thereof; and,
   a plasticizer selected from the group consisting of polyhydric alcohols, polyethylene glycols, sorbitol, water, and mixtures thereof.

10. The adhesive of claim 1, wherein said adhesive further comprises at least one lipid micelling polymer.

11. The adhesive of claim 10, wherein said lipid micelling polymer is an alternating polymer of styrene and maleic anhydride.

12. An adhesive of claim 1, wherein said adhesive further comprises a surfactant.

13. The adhesive of claim 12, wherein said surfactant comprises at least one propylene oxide/ethylene oxide block copolymer.

14. The adhesive of claim 1, wherein said hydrophilic component is selected from the group consisting of 2-acrylamido methylpropane sulphonic acid, (acrylic 3-sulphopropyl ester) acid, salts thereof, and combinations thereof; and,
   wherein said hydrophobic component selected from the group consisting of acrylamide, acrylonitrile, methylacrylate, ethylacrylate, butylacrylate, vinyl ethers, vinylpyrrolidine, glycidyl acrylate, methyl acrylate, hydroxyethylacrylate, hydroxypropylacrylate, and combinations thereof.

15. The adhesive of claim 1, wherein said adhesive covers at least a portion of a release liner.

16. The adhesive of claim 15, wherein said adhesive is coextensive with said wearing facing surface of said topsheet and said release liner.

* * * * *